United States Patent [19]

Melvin, Jr.

[11] 4,176,196

[45] Nov. 27, 1979

[54] HYPOGLYCEMIC ARYLCYCLOHEXANE ACETIC ACIDS

[75] Inventor: Lawrence S. Melvin, Jr., Gales Ferry, Conn.

[73] Assignee: Pfizer Inc., New York, N.Y.

[21] Appl. No.: 848,537

[22] Filed: Nov. 4, 1977

[51] Int. Cl.$^2$ .................. A01K 31/19; A01K 31/215; C07C 69/76

[52] U.S. Cl. .................................... 424/308; 424/317; 424/324; 250/559 R; 560/59; 560/61; 562/469; 562/492

[58] Field of Search ................ 562/469, 492; 424/305, 424/308, 317, 324; 560/59, 61; 260/559 R

[56] References Cited

U.S. PATENT DOCUMENTS

| 3,027,302 | 3/1962 | Carissimi et al. | 424/317 |
| 3,778,442 | 12/1973 | Turbanti | 562/492 |
| 3,947,588 | 3/1976 | Sherlock et al. | 424/317 |
| 4,007,282 | 2/1977 | Manz et al. | 424/317 |

OTHER PUBLICATIONS

Dave, Vinod et al., "On The Putative Formation of Stable Enols," Tetrahedron Letters No. 51, pp. 4695–4696 (1976).

Menger, Fredric M., et al., "Organic Chemistry," pp. 187–188 (1972), W. A. Benjamin, Inc. Publ.

Hass, Georges et al., "Cyclohexenyl Compounds," Ger. Offen. 2,436,617, Feb. 27, 1975, (See Chemical Abstracts 83 (1975) #131,220h).

*Primary Examiner*—James O. Thomas, Jr.
*Assistant Examiner*—L. Hendriksen
*Attorney, Agent, or Firm*—Francis X. Murphy; Charles J. Knuth; Peter C. Richardson

[57] ABSTRACT

Novel hypoglycemic agents comprising 3-hydroxy-3-arylcyclohexane-1-acetic acid, 3-arylcyclohexene-1-acetic acids and derivatives thereof are disclosed.

5 Claims, No Drawings

HYPOGLYCEMIC ARYLCYCLOHEXANE ACETIC ACIDS

BACKGROUND OF THE INVENTION

This invention relates to new and useful 3-hydroxy-3-aryl cyclohexane-1-acetic acids, 3-arylcyclohexene-1-acetic acids and derivatives thereof which are useful for reducing blood sugar levels in warm blooded animals. More particularly, these compounds are useful for therapeutic use as hypoglycemic agents in the treatment of diabetes.

In the past, many attempts have been made to obtain new hypoglycemic agents. Generally these attempts have involved synthesis of various sulfonylureas, biguanidine derivatives and related compounds.

3-Hydroxy-3-(p-methoxyphenyl)-cyclohexane-1-acetic acid and 3-(p-methoxyphenyl)-cyclohexene-1-acetic acid have been described by Dave and Warnhoff, Tetrahedron Letters, 1976 No. 51, 4695 (1976). Previously, Dabral et al., Tetrahedron Letters 1975, No. 52, 4681 (1975) had described the formation of a compound to which they attributed the formula

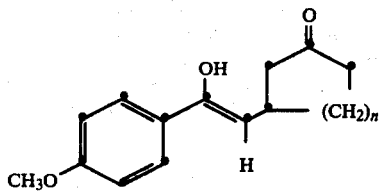

where n is 1 or 2. However, Dave and Warnhoff, supra, suggest that Dabral et al. erroneously attributed this formula to the compound obtained and that the compound produced was in fact 3-(p-methoxyphenyl)-cyclohexene-1-acetic acid. This has been confirmed in the course of the work relating to the present invention.

SUMMARY OF THE INVENTION

It has now been found that certain 3-hydroxy-3-arylcyclohexane-1-acetic acids, 3-arylcyclohexene-1-acetic acids and derivatives thereof are useful for lowering blood sugar levels in warm blooded animals and can be used as hypoglycemic agents for the treatment of diabetes.

The 3-hydroxy-3-arylcyclohexane-1-acetic acids and derivatives thereof of the present invention are those of the formula

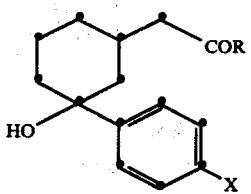

wherein R is selected from —OR$_1$ and —NH$_2$; X is selected from hydrogen and —OR$_1$, wherein R$_1$ is selected from hydrogen and alkyl of 1 to 4 carbon atoms, and the pharmaceutically acceptable salts of those compounds wherein R is —OH. Preferred compounds are those wherein R is —OH and those wherein the group X is hydrogen, hydroxy or methoxy. Especially preferred are the compounds wherein R is hydroxy and X is hydrogen and where R is hydroxy and X is methoxy.

Compounds of formula I are also useful intermediates for the formation of the novel 3-arylcyclohexene-1-acetic acids and derivatives thereof as hereinafter disclosed.

The novel 3-arylcyclohexene-1-acetic acids and derivatives thereof of the present invention are those selected from those of the formulae

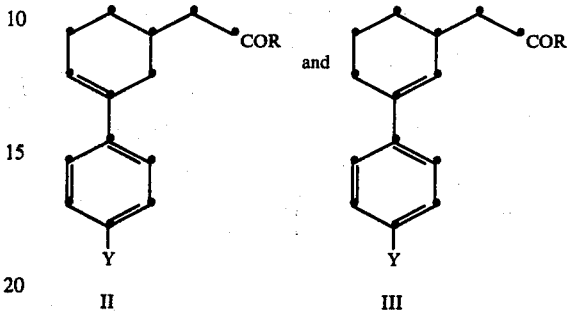

wherein R is selected from —OR$_1$ and —NH$_2$, wherein R$_1$ is selected from hydrogen and alkyl of 1 to 4 carbon atoms and where Y is selected from hydrogen and —OH, and the pharmaceutically acceptable salts of those compounds wherein R is —OH. Preferred compounds are those wherein the group R is —OH and those wherein Y is hydroxy. Especially preferred are those compounds of formula II. Compounds of particular interest are those compounds of formula II wherein R is —OH and wherein Y is hydrogen.

Also disclosed is a method for lowering the blood sugar level in the treatment of a diabetic subject which comprises administering to the subject an effective blood sugar lowering amount of a compound of formula I. Preferred methods are those employing the preferred compounds of formula I as described above herein.

Also disclosed is a method for lowering blood sugar level in the treatment of a diabetic subject which comprises administering to the subject an effective blood sugar lowering amount of a compound selected from those of the formulae

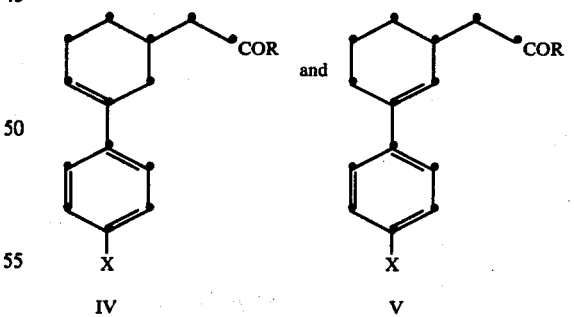

wherein R is selected from —OR$_1$ and —NH$_2$; X is selected from hydrogen and —OR$_1$ and R$_1$ is selected from hydrogen and alkyl of one to four carbon atoms, and the pharmaceutically acceptable salts of those compounds wherein R is —OH.

Also disclosed are pharmaceutical compositions comprising a pharmaceutically acceptable carrier and an effective blood sugar lowering amount of a compound selected from those of the formulae I, IV or V. Preferred pharmaceutical compositions are those containing the preferred compounds of the present invention as previously described herein.

DETAILED DESCRIPTION OF THE INVENTION

The 3-hydroxy-3-arylcyclohexane-1-acetic acids of the present invention are readily prepared by the reaction of 3-oxo-cyclohexane-1-acetic acids, prepared by the method of Bartlett and Woods, J.A.C.S., 62, 2933 (1940) and an appropriate aryl magnesium halide Grignard reagent, for example phenyl magnesium bromide, p-anisylmagnesium bromide and the like, depending on the desired aryl substituent. For compounds where the group X is hydroxy, the hydroxy group in the starting material should first be protected by a group readily removed at a later stage in the synthesis for example by making the corresponding benzyl ether. The reaction is conducted in a reaction inert organic solvent, typically an ether such as diethyl ether, tetrahydrofuran or dimethoxyethane at temperatures in the range of about −10° C. to about 50° C., preferably at about 10° C. to about 25° C. For compounds where X is hydroxy the protecting group employed during the above reaction is then removed by hydrolysis, using acid or catalytic hydrogenation. The 3-hydroxy-3-arylcyclohexane-1-acetic acid is formed as a mixture of diastereomers, which may be separated by extraction and crystallization if desired. In the specification and claims hereof it is intended to include both of these diastereomers and mixtures thereof.

The 3-hydroxy-3-arylcyclohexane-1-acetic acids formed as described above may be used to prepare the corresponding 3-arylcyclohexene-1-acetic acids of the present invention. The appropriate 3-hydroxy-3-arylcyclohexane-1-acetic acid, either as one of the diastereomers or a mixture thereof, is heated with a strong acid at temperatures between about 50° C. and 150° C., preferably at reflux temperature. The reaction is conducted in a solvent such as water, benzene or toluene. Suitable acids include, but are not limited to, hydrochloric acid, sulfuric acid, p-toluene sulfonic acid and sulfonic ion exchange resins. The 3-arylcyclohexene-1-acetic acid is obtained as a mixture of the two isomers as represented in formulae II and III i.e. 3-aryl-3-cyclohexene-1-acetic acid and 3-aryl-2-cyclohexene-1-acetic acid, respectively. These isomers may be separated if desired or can be used as a mixture of the two isomers. Separation of the isomers may be effected, for example, by fractional crystallization and column chromatography.

The 3-arylcyclohexene-1-acetic acids of this invention may also be prepared from diones of the formula

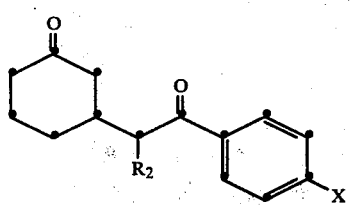

where $R_2$ is hydrogen or $-CO_2R_3$ where $R_3$ is alkyl of one to four carbon atoms and X is as previously defined. Compounds where $R_2$ is hydrogen are prepared by the method of Narasaka et al., Bull. Chem. Soc. Japan, 49, 779 (1976). Compounds where $R_2$ is $-CO_2R_3$ are prepared by the addition of one equivalent of 2-cyclohexen-1-one at 0° to 25° to one equivalent of an appropriate alkyl aroyl acetate, such as ethylbenzoyl acetate, ethyl 4-hydroxybenzoyl acetate and the like, in a hydrocarbon solvent such as benzene or toluene containing approximately 0.1 equivalent of an alkali metal hydride such as sodium hydride. Conversion of the dione to a 3-arylcyclohexen-1-acetic acid may be effected by heating the dione at a temperature between about 50° C. and 150° C., preferably at reflux temperature, in the presence of a strong acid such as hydrochloric acid, sulfuric acid, paratoluenesulfonic acid or sulfonic ion exchange resins. The reaction is conducted in a suitable solvent, for example, water benzene or toluene.

The acids formed above can be readily converted to the corresponding esters, amides and to the pharmaceutically acceptable salts of these acids by means known in the art. Thus, for example esterification can be effected by reaction of the acid with the appropriate alkanol of one to four carbon atoms, or by reaction with a suitable diazoalkane. The amides may be formed by the reaction of the ester with ammonia or by conversion of the acid to the acid chloride followed by ammonolysis. Suitable pharmaceutically acceptable salts of those compounds where R is $-OH$ include, but are not limited to, those having a counterion selected from an alkali metal, such as sodium, lithium or potassium, an alkaline earth metal such as calcium or magnesium, and ammonium.

The compounds of the present invention are useful for lowering blood sugar levels in warm blooded animals and are useful in therapeutic applications as hypoglycemic agents for the treatment of diabetes. An effective amount of a compound of formulae I, IV or V is administered to the subject in need of treatment using conventional routes of administration. Oral administration is a preferred route. The effective dosage required for oral administration will be from about 5 to 200 mg/kg body weight of the subject to be treated. The physician will in any event determine the particular dosage for the individual patient. The compounds can be used either alone or in combination with pharmaceutically acceptable carriers and may be used in either single or multiple doses. More particularly, the compounds can be administered in a wide variety of dosage forms by combination with various inert pharmaceutically acceptable carriers in the form of tablets, lozenges, powders, capsules, suspensions, syrups and the like. Suitable carriers include inert solid diluents or fillers, sterile aqueous solutions and non-toxic organic solvents. These pharmaceutical compositions may, if desired, contain additional substances such as flavoring agents, binding agents, coating agents and the like.

The present invention is illustrated by the following examples. It should be understood, however, that the invention is not limited to the specific details of these examples.

EXAMPLE 1

3-Hydroxy-3-phenylcyclohexane-1-acetic acid

To a solution of 80 mmol of phenyl magnesium bromide (from 24.2 ml of a 3.3 M solution of phenyl magnesium bromide in ether) in 100 ml of tetrahydrofuran at 10° C. was slowly added 5.0 g (32.1 mmol) of 3-oxocyclohexane-1-acetic acid (prepared by the method of Bartlett and Woods, J.A.C.S. 62, 2933 (1960)) in 25 ml of tetrahydrofuran. The reaction was stirred 1 hr. longer at 25° and then added to 250 ml 1 N hydrochloric acid and 250 ml ether. The organic extract was extracted with 150 ml of 1 N sodium hydroxide. The base extract was reacidified with 200 ml of 1 N hydrochloric acid and extracted with 300 ml of ether. This ether extract was dried over magnesium sulfate and evaporated to an oil. Crystallization from ether gave 3.25 g (43%) of the title compound, MP, 152°, as a pure diastereomer. The mother liquor (4.0 g, 53%) was pure by PMR analysis and contained the other diastereomer. Crystallization of the mother liquor in cyclohexane followed by several recrystallizations gave the other diastereomer of the title compound, MP, 114°–115°.

MP, 152° Diastereomer:

PMR: $\delta_{CDCl_3\text{-}D_6DMSO}^{TMS}$ 0.9–2.0 (m), 2.0–2.5 (m) and 7.2–7.7 (m).

IR: (KBr) 3436, 3000 and 1718 cm$^{-1}$.

MS: m/e 234(M+), 216, 205, 191, 188, 175, 173, 145, 133, 131, 120 and 105.

Analytical Calc'd. for $C_{14}H_{18}O_3$: C, 71.77; H, 7.74; Found: C, 71.66; H, 7.73.

MP, 114°–115° Diastereomer:

PMR: $\delta_{CDCl_3\text{-}D_6DMSO}^{TMS}$ 0.9–2.1 (m), 2.1–2.5 (m) and 7.2–7.7 (m).

IR: (KBr) 3484, 3000 and 1718 cm$^{-1}$.

MS: m/e 234 (M+), 216, 191, 188, 175, 173, 157, 145, 133, 131, 120 and 105.

Analysis: Anal. Calc'd. for $C_{14}H_{18}O_3$: C, 71.77; H, 7.74. Found: C, 71.85; H, 7.71.

By use of appropriately substituted aryl magnesium bromides, the other compounds of this invention may be prepared following the methods of the above example.

EXAMPLE 2

3-Phenyl-3-cyclohexene-1-acetic acid and 3-Phenyl-2-cyclohexene-1-acetic acid

A mixture of 500 mg (2.13 mmole) of 3-hydroxy-3-phenylcyclohexane-1-acetic acid (isomer of MP 152°) and 50 ml of 3 N hydrochloric acid was heated at reflux for 45 min. The reaction was cooled, saturated with sodium chloride and extracted with three 100 ml. portions of ether. The combined ether extract was dried over magnesium sulfate and evaporated to give a quantitative yield of the title compound as a 68:32 mixture of the 3-cyclohexene:2-cyclohexene isomers, as indicated by 100 MHz PMR analysis. The lower melting isomer of 3-hydroxy-3-phenylcyclohexane-1-acetic acid can also be used in this reaction.

Fractional crystallization from cyclohexane of the mixture of isomers obtained from the above reaction yields (30–50%) the pure 3-cyclohexene isomer MP 85°–6° (from cyclohexane and/or diisopropyl ether). Column chromatography of the mother liquor on silica gel eluted with 1:1 ether: cyclohexane yields the 2-cyclohexene isomer (as an oil) contaminated with approximately 25% of the 3-cyclohexene isomer.

3-Phenyl-3-cyclohexene-1-acetic acid:

PMR: (100 MHz) $\delta_{CDCl_3}^{TMS}$ 1.09–2.97 (m), 6.09 (m, vinyl proton), 7.07–7.49 (m, ArH) and 10.94 (S, COOH).

IR: (CHCl$_3$) 3000, 1718 and 1653 cm$^{-1}$.

UV: $\lambda_{Max}^{Ethanol}$ 247 nm (E=11,500).

MS: m/e (% intensity) 216.1147 (43, M+), 157.1004 (92) and 156.0934 (100).

Analysis: Anal Calc'd. for $C_{14}H_{16}O_2$: C, 77.75; H, 7.46; Found: C, 77.65; H, 7.62.

3-Phenyl-2-cyclohexene-1-acetic acid:

PMR: (100 MHz) $\delta_{CDCl_3}^{TMS}$ 1.07–3.05 (m), 5.96 (m, vinyl proton), 7.07–7.67 (m, ArH) and 10.69 (S, COOH).

Likewise, the other 3-hydroxy-3-arylcyclohexane-1-acetic acids prepared by the method of Example 1 may be converted to the corresponding 3-arylcyclohexene-1-acetic acids by the method of Example 2.

EXAMPLE 3

3-Phenyl-3-cyclohexene-1-acetic acid and 3-Phenyl-2-cyclohexene-1-acetic acid

The title compounds were also prepared by the following method:

A mixture of 500 mg (2.31 mmol) of α-(3-oxocyclohexyl)acetophenone (prepared by the method of Narasaka et al, Bull. Chem. Soc. Japan, 49, 779 (1976)) in 50 ml of 3 N hydrochloric acid was heated at reflux for 4 hr. The reaction was cooled, saturated with sodium chloride and extracted with three 100 ml portions of ether. The combined ether extract was dried over magnesium sulfate and evaporated to yield 372 mg (74%) of the title compound as a 65:35 mixture of the 3-cyclohexene: 2-cyclohexene isomers as indicated by 100 MHz PMR analysis of the crude reaction product.

EXAMPLE 4

Ethyl benzoyl-(3-oxocyclohexyl)acetate

To a suspension of 60 mg (0.0025 mole) of sodium hydride in 7 ml of toluene was added 4.32 ml (0.025 mole) of ethyl benzoyl acetate. After several minutes a solution was obtained to which was added 2.41 ml (0.025 mole) of cyclohexenone. The reaction was stirred 36 hrs. at room temperature and then added to 25 ml 1 N hydrochloric acid—25 ml saturated sodium chloride—150 ml ether. The ether extract was dried over magnesium sulfate and evaporated to an oil. This crude oil was purified via column chromatography on 300 g of silica gel eluted with 50% ether—pentane to yield 4.8 g (67%) of the title compound as an oil.

PMR: $\delta_{CDCl_3}^{TMS}$ 1.20 (t, J=7 Hz, methyl of ethyl ester), 4.20 (d, J=7 Hz, methylene of ethyl ester), 4.42 (d, J=2 Hz, acetate methine), 7.5 (m, ArH) and 8.0 (m, Arh).

EXAMPLE 5

3-phenyl-3-cyclohexene-1-acetic acid and 3-phenyl-2-cyclohexene-1-acetic acid

A mixture of 500 mg (1.73 mmol) of ethyl benzoyl-(3-oxocyclohexyl)acetate and 50 ml of 3 N hydrochloric acid was heated at reflux for 4 hrs. The reaction was cooled, saturated with sodium chloride and extracted with three 100 ml portions of ether. The combined extract was dried over magnesium sulfate and evaporated to a quantitative yield of the title compound as a 65:35 mixture of the 3-cyclohexene: 2-cyclohexene isomers as indicated by 100 MHz PMR analysis of the crude reaction product.

EXAMPLE 6

The ability of the compounds of the present invention to lower blood sugar levels has been determined in the following test:

Male Charles River Sprague-Dawley CD rats, fasted for 24 hours, 160–220 g, were dosed with the test compound at 50, 100 or 150 mg/kg body weight in saline solution containing glucose at 1 g/kg body weight, administered intraperitoneally. Control animals received saline containing glucose at 1 g/kg only. Tail blood samples were taken at 0, 0.5, 1, 2 and 3 hours post-treatment. Blood glucose was determined by ferricyanide reduction using a Technicon Auto-Analyser. The results obtained are shown in Table 1. Results are the mean of 5 animals per group ± standard error.

Table 1

| Compound | Dose mg/kg | Blood Glucose (mg/dL) Hours after treatment | | | | |
|---|---|---|---|---|---|---|
| | | 0 | .5 | 1 | 2 | 3 |
| 3-hydroxy-3-phenylcyclo-hexane-1-acetic acid (m.p. 152° Diastereomer) | 100 | 75±1 | 137±3 | 97±4 | Θ±2 | 59±2 |
| Control | | 76±5 | 130±7 | 118±5 | 94±3 | 83±2 |
| 3-hydroxy-3-phenylcyclo-hexane-1-acetic acid (m.p. 152° Diastereomer) | 50 | 62±1 | 128±4 | 107±4 | 77±2 | 70±5 |
| | 150 | 69±1 | 116±2 | 97±3 | 67±2 | 57±1 |
| Control | | 70±2 | 123±4 | 111±5 | 84±2 | 84±2 |
| 3-hydroxy-3-phenylcyclo-hexane-1-acetic acid (m.p. 114–115° Diastereomer | 100 | 65±1 | 129±6 | 95±3 | 74±2 | 74±3 |
| Control | | 72±2 | 138±4 | 112±3 | 90±4 | 83±4 |
| 3-phenyl-3-cyclohexene-1-acetic acid | 100 | 71±2 | 113±4 | 85±3 | 78±3 | 76±2 |
| Control | | 73±3 | 123±5 | 99±2 | 79±3 | 81±3 |
| 3-(p-methoxyphenyl)-3-cyclohexene-1-acetic acid | 100 | 65±1 | 133±6 | 84±3 | 72±2 | 72±3 |
| Control | | 72±2 | 138±4 | 112±3 | 90±4 | 83±4 |

What is claimed is:

1. A method for lowering blood sugar in the treatment of a diabetic subject, which comprises administering to said subject an effective blood sugar lowering amount of a compound of the formula

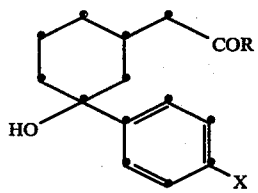

I wherein R is selected from —OR$_1$ and —NH$_2$;
X is selected from hydrogen and —OR$_1$;
R$_1$ is selected from hydrogen and alkyl of 1 to 4 carbon atoms;
and the pharmaceutically-acceptable salts of those compounds wherein R is —OH.

2. The process of claim 1 wherein R is —OH and X is hydrogen.

3. A method for lowering blood sugar in the treatment of a diabetic subject, which comprises administering to said subject an effective blood sugar lowering amount of a compound selected from those of the formulae

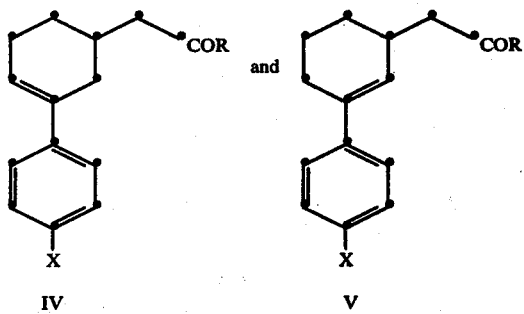

IV  V wherein R is selected from —OR$_1$ and —NH$_2$;
X is selected from hydrogen and —OR$_1$;
R$_1$ is selected from hydrogen and alkyl of 1 to 4 carbon atoms;
and the pharmaceutically-acceptable salts of those compounds wherein R is —OH.

4. The method of claim 3 wherein R is —OH and X is hydrogen.

5. The method of claim 4 wherein the compound is of formula IV.

* * * * *